US009164073B1

(12) United States Patent
Nosovitskiy et al.

(10) Patent No.: US 9,164,073 B1
(45) Date of Patent: *Oct. 20, 2015

(54) MULTI-FUNCTIONAL, DISCRETE DETERMINATION OF CONCENTRATIONS OF GASES IN A GASEOUS MIXTURE

(76) Inventors: Pavel Nosovitskiy, Walnut Creek, CA (US); Gennadiy Nosovitskiy, Round Lake, IL (US)

( * ) Notice: Subject to any disclaimer, the term of this patent is extended or adjusted under 35 U.S.C. 154(b) by 657 days.

This patent is subject to a terminal disclaimer.

(21) Appl. No.: 13/471,310

(22) Filed: May 14, 2012

Related U.S. Application Data

(63) Continuation-in-part of application No. 12/322,989, filed on Feb. 10, 2009, now Pat. No. 8,185,325.

(60) Provisional application No. 61/065,458, filed on Feb. 11, 2008.

(51) Int. Cl.
*G01N 31/00* (2006.01)
*G11C 17/00* (2006.01)
*G06F 15/00* (2006.01)
*G01N 33/00* (2006.01)

(52) U.S. Cl.
CPC .................................. *G01N 33/0031* (2013.01)

(58) Field of Classification Search
None
See application file for complete search history.

(56) References Cited

U.S. PATENT DOCUMENTS

| | | | |
|---|---|---|---|
| 4,706,493 A | 11/1987 | Chang | |
| 4,941,897 A | 7/1990 | Vann, III | |
| 5,174,044 A | 12/1992 | Jacobs | |
| 5,327,901 A | 7/1994 | Delente | |
| 5,602,326 A | 2/1997 | Takahashi | |
| 6,046,054 A | 4/2000 | McGeehin et al. | |
| 6,076,392 A | 6/2000 | Drzewiecki | |
| 6,128,945 A | 10/2000 | Shioiri | |
| 6,312,390 B1 | 11/2001 | Phillips | |
| 6,540,691 B1 | 4/2003 | Phillips | |
| 6,620,107 B2 | 9/2003 | Payne | |
| 6,673,644 B2 | 1/2004 | Gole | |
| 6,712,770 B2 | 3/2004 | Lin | |
| 6,726,637 B2 | 4/2004 | Phillips | |
| 6,792,793 B2 | 9/2004 | Mendoza | |
| 6,837,095 B2 | 1/2005 | Sunshine | |
| 6,849,239 B2 | 2/2005 | Morris | |
| 6,960,476 B2 | 11/2005 | Morris | |
| 6,974,706 B1 | 12/2005 | Melker | |
| 7,004,909 B1 | 2/2006 | Pattel | |
| 7,076,371 B2 | 7/2006 | Fu | |
| 7,153,272 B2 | 12/2006 | Talton | |
| 7,239,905 B2 | 7/2007 | Kiani-Azarbayjany | |
| 7,248,905 B2 | 7/2007 | Fukuda | |
| 7,308,293 B2 | 12/2007 | Gerlitz | |
| 7,353,152 B2 | 4/2008 | Brazhnik | |
| 7,356,420 B2 | 4/2008 | Vilanova | |
| 7,421,882 B2 | 9/2008 | Leddy | |
| 7,438,855 B2 | 10/2008 | Sota | |
| 7,454,296 B2 | 11/2008 | Wang | |
| 7,460,958 B2 | 12/2008 | Walsh | |
| 7,461,540 B2 | 12/2008 | Monkemoller | |
| 7,473,229 B2 | 1/2009 | Webber | |
| 8,185,325 B2* | 5/2012 | Nosovitskiy et al. | ........... 702/24 |
| 2005/0072213 A1* | 4/2005 | Besnard et al. | .............. 73/31.06 |

OTHER PUBLICATIONS

Schiffman et al. Analysis of Medication Off-odors Using an Electronic Nose Chem. Senses vol. 22, pp. 119-128 (1997).*
Comini, E., Fagila, G., Sberveglieri, G. "Stable and highly sensitive gas sensors based on semiconducting oxide nanobelts." Applied Physics Letters 81.10(2002). New York.
Deininger, Williams, and Kostelecky. "Solid State Sensors for Nox Detection." ISA Expo 2003 Technical Conference. Houston, TX, US.
Figaro General Information for TGS Sensors: Technical Information on Usage of TGS sensors for Toxic and Explosive Gas Leak Detectors. Figaro USA Inc, 2004. Glenview, IL, US.
Galeazzo, Peres, Ramirez-Fernandez. "Analysis of Porous Silicon Devices for Gas Sensors." SIM Group, Polytechnic Institute, University of San Paulo, 2001. San Paulo, BR.
Harsanyi. "Sensors in Biomedical Applications: Fundamentals, Technology and Applications." CRC Press. 2000. NewYork, NY, US.
Kawi, Li, Gao."Development of Novel Semiconductor Oxide Gas Sensors." PAO Enterprises. 1998. SG.
Loginov, Rembeza, Svistova, and Shcherbakov. "Effect of laser treatment on the gas sensitivity of tin dioxide films." Technical Physics Letters 24.4 (1998): 270-271. New York.
Ma, Wang, Liao, Kong. "Study on Sensitivity of Nano-grain ZnO Gas Sensors." Journal of Wide Bandgap Materials 2002:10:113. Thousand Oaks, CA, US.
Rand, Richard. "Lecture Notes on Non-Linear Vibrations." Department of Theoretical and Applied Mechanics. Cornell University. Ithaca, NY, US.
Sakai, Motooka, Miura, and Yamazoe. "Thin-film-type oxide semiconductor sensor for detecting acetone in human expiration aiming at diagnosis of diabetes." Kuyushu University.
Ping, "A novel method for diabetes diagnosis based on electronic nose," Biosensors & Bioelectronics, vol. 12, No. 9-10, pp. 1031-1036 (1997).
Houtman, Every Breath You Take: Looking for a Chemical Fingerprint in Human Breath: UMaine Magazine Today. University of Maine 2002. Orono, ME, US.
Malkin. Theory of Stability of Motion. United States Atomic Energy Commission. 1952. Washington D.C., US.

(Continued)

*Primary Examiner* — John S Brusca
(74) *Attorney, Agent, or Firm* — John Chandler (57) ABSTRACT

Method and device for detection and quantitative and qualitative analysis of components in a gaseous mixture distinguished by high selectivity and high resolution. Method allows to distinguish the influence of individual gases, by themselves or in a mixture, on the microstructure of a sensor's sensitive layer and utilizing the variations of measured parameters to analyze and derive the characteristics of gases, for example, the concentration of a gas or multiple gases in a mixture. As an example, the method could be utilized in medicine for non-invasive detection of the blood glucose level in diabetics. Device realizing the method is described.

20 Claims, 6 Drawing Sheets

(56) References Cited

OTHER PUBLICATIONS

Neamen. Semiconductor Physics and Devices, 14-page excerpt, 3rd Edition. McGraw Hill. 2003. New York, NY, US.

Risby. "Current status of clinical breath analysis." Applied Physics B: Lasers and Optics 85 (2006): 421-26. New York, NY, US.

Van Valkenburg. Reference for Engineers Radio. Electronics, Computer and Communications. 9th Edition. Butterwoth-Heinemann. 2002. Boston. Massachusetts, US.

* cited by examiner

Transition curves in Mathieu's equation. S=stable, U=unstable.

MULTI-FUNCTIONAL, DISCRETE DETERMINATION OF CONCENTRATIONS OF GASES IN A GASEOUS MIXTURE

CROSS-REFERENCE TO RELATED APPLICATIONS

For purposes of the USPTO extra-statutory requirements, the present application constitutes a continuation-in-part of U.S. patent application Ser. No. 12/322,989 filed 10 Feb. 2009, which is currently co-pending, or is an application of which a currently co-pending application is entitled to the benefit of the filing date. Said '989 application claims priority to a U.S. provisional application having Ser. No. 61/065,458 which was filed 11 Feb. 2008.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette 18 Mar. 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications.

Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s). All subject matter of the Related Applications and of any and all parent, grandparent, great-grandparent, provisional, etc. applications of the Related Applications is incorporated herein by reference to the extent such subject matter is not inconsistent herewith. Where there is determined to be a conflict, the subject matter and description described herein controls.

BACKGROUND

1. Field of the Invention

The invention relates to measuring and testing, particularly for gas analysis, for example breath analysis of organisms and subclasses of breath analysis inside the body. The invention relates to chemistry, particularly in analytical and immunological testing.

2. Description of Related Art

Currently, a number of marker molecules have been identified in breath that could be used to identify disease, disease progression, or to monitor therapeutic intervention and this list is expected increase dramatically since the analysis of breath is ideally suited for population-based studies in the developed and underdeveloped world.

The concept that blood, urine, and other body fluids and tissues can be collected and analyzed to yield information for diagnosis of disease states or to monitor disease progression and/or therapy is the foundation of modern medicine.

However, the use of breath as a collectable sample has not received comparable clinical use, as conducted studies have only been possible so far as a result of enhanced separation of gaseous molecules by gas chromatography, increased selectivity of mass or optical spectrometers and improved limits of detection from high parts-per-million to parts-per-billion.

Breath measurement has enormous potential, in part because of its inherent safety. The only requirement to collect a breath sample is that the subject must be breathing (spontaneously or mechanically supported). Breath analysis can be used to detect disease, monitor disease progression, or monitor therapy.

Recent advances in instrumentation may enable more of this potential to be realized. In particular, the wider availability of real-time, portable monitors would be a breakthrough.

It was discovered decades ago that atoms and molecules interacting with semiconductor surfaces influence surface properties of semiconductors, such as conductivity and surface potential. Seiyama (1962) and Taguchi (1970) first applied the discovery to gas detection by producing the first chemo-resistive, semiconductor gas sensors. Since then, semiconductor gas sensors have been widely used as domestic and industrial gas detectors for gas-leak alarms, process control, pollution control, etc.

Recent years have seen the introduction of solid-state sensors for the detection of different gases, which are based on metal oxide semiconductors. As with catalytic devices, which rely on the absorption of a gas on to a heated oxide surface, the absorption and/or subsequent reaction of a gas on the surface of the oxide produces an electrical conduction change in the metal-oxide itself on the account of the electronic processes involved in the reaction on its surface.

These conductivity changes relate to the amount of gas absorbed on the surface of the oxide and hence to its concentration in the surrounding atmosphere.

The metal-oxide semiconductor sensor is comprised of a tin oxide that is sintered on a small ceramic tube or surface. A coiled wire is placed through the center of the ceramic tube to act as the sensor's heater. Metal wires provide electrical contact between the tin oxide and the rest of the electronics.

The metal-oxide sensor requires between 300 mW and 600 mW of power to operate the sensor at elevated temperature between 300 and 450 degrees Celsius.

The combination of the sensor's operating temperature and composition of the metal-oxide yields different responses to various gases.

When a metal-oxide crystal, such as $ZnO_2$, is heated at a certain high temperature in the air, oxygen is adsorbed on the crystal surface with a negative charge. Then, the donor electrons in the crystal surface are transferred to the adsorbed oxygen, resulting in a removal of positive charges in a space charge layer. This surface potential is formed to serve as a potential barrier against electron flow.

Inside the sensor, electric current flows through the conjunction part (drain boundary) of $ZnO_2$ micro-crystals. At drain boundaries, adsorbed oxygen forms a potential barrier, which prevents carriers from moving freely.

The electrical resistance is attributed to this potential barrier. In the presence of a deoxidizing gas, the surface density of the negatively charged oxygen decreases, thus the barrier height in the drain boundary is reduced. The reduced barrier height decreases the sensor's resistance.

The relationship between the resistance of the sensor and the concentration of the deoxidizing gas can be expressed by the following equation over a certain range of gas concentration:

$$Rs = A*[C]*(-x) \qquad \text{(Equation 1)}$$

Where Rs=electrical resistance of the sensor, A=constant, [C]=gas concentration, and (-x)=slope of the Rs curve.

According to Equation 1, the relationship of the sensor's resistance to gas concentration is generally linear on a logarithmic scale within a practical range, determined by current market data and depending from the particular gas, to be from approximately a hundred ppm (parts per million) to several thousand ppm of gas concentration.

Modern metal-oxide methods and the method of preparing a sensitive surface with a laser may resemble the method introduced in the invention. For example, a semiconductor oxide gas sensor was introduced through a research team led by Dr. S. Kawi from the department of chemical engineering of the National University of Singapore (NUS). However, researchers indicated that more extensive experimentation was necessary to understand the nature of the involved processes and explain the achieved results.

Another method to improve the quality and sensitivity of the $ZnO_2$ layer to tens of ppm is the method of using a laser to scan the sensor's surface. By using a laser, it is possible to change the density of the electrical charge on the sensor's sensitive layer.

The above-described methods and techniques have several disadvantages in common and cannot be used for investigations of gaseous mixtures with low concentration levels.

The use of Equation 1 can be limiting and becomes invalid for small concentrations of a gas because at low concentration levels, changes in the resistivity also occur under the influence of internal factors, such as diffusion and recombination, which are not taken into account by the formula.

The dependency on a logarithmic relationship derived from Equation 1 does not allow for selectively analyzing the effect of similar gaseous components on the semiconductor's sensing layer.

In the presence of destabilizing factors, such as a change in the temperature or a change in the flow of gas, the formula can no longer be applied. Consequently, the destabilizing factors are prevalent at small concentrations.

SUMMARY OF THE INVENTION

Some of the advantages and objectives of the invention are as follows: (1) provide a method to detect, measure and monitor small concentrations of individual gases or gases in a gaseous mixture with high selectivity and high sensitivity; and (2) provide an instrument for various applications such as an accurate, non-invasive monitoring and diagnostic of pulmonary exclusions.

The invention may be used for gas analysis such as in medicine, defense and military industries and food industries. In general, the invention may be used to determine quantitative and qualitative characteristics of components in a gaseous mixture with a high degree of selectivity and resolution.

The invention, which includes methods and devices for detection and quantitative and qualitative analysis of components in a gaseous mixture, distinguished by high selectivity and high resolution, allows one to discriminate the influence of individual gases, by themselves or in a mixture, on the microstructure of a sensor's sensitive layer. The invention can use this influence to analyze and derive parameters related to gases, thus bypassing limitations imposed by traditional measuring and monitoring techniques. The invention provides effective alternatives in areas such as disease diagnostics and other areas and applications that previously have not been accessible or attainable with known practices.

In another aspect of the invention, a model and a new process for determining the characteristics of various components within gaseous mixtures is disclosed. The invention involves or includes sensitive and selective measurement of individual gases within mixtures.

In another aspect of the invention, the methods disclosed are distinguished from other methods by high sensitivity and high selectivity and locates domains of dynamic stability and instability.

In another aspect of the invention, the methods are capable of determining boundaries of the domains of dynamic stability, where measurements can be extracted and domains of instability, where measurements cannot be predicted. Destabilizing factors, such as temperature or pressure fluctuations, which hinder measurements and deform the domains' boundaries, are taken into account.

In another aspect of the invention, since the domains of stability and instability possess varying widths and can be regulated by changing certain parameters of the system, the method provides the technique to reach desired domains for different applications.

In another aspect of the invention, a class of algorithms may be used with the disclosed methods for the detection of individual components with very similar characteristics in gaseous mixtures through comparison of locations of individual domains of stability and instability, which are not identical within the measurement diapason.

These and other aspects and features of the invention will be more fully apparent from the following description and appended claims taken in conjunction with the accompanying figures.

BRIEF DESCRIPTION OF THE DRAWINGS

FIG. 1 shows a sensing mechanism in solid-state metal-oxide sensors according to one implementation of the invention.

DETAILED DESCRIPTION

By using the methodology described herein, it is possible to detect relatively low concentrations (e.g., tens ppm, hundreds ppb) of reducing gases and, with some applied limitations, and selectively distinguish certain gases, vapors or liquids from one another.

The functioning of sensors and calculation of their parameters may be observed during a state of dynamic equilibrium. In a steady state, any small variation or oscillation surrounding the predominant average value are deemed insignificant and are thrown out from the calculation. As a result, limitations occur and the sensor's output parameters are only predictable and calculated for a particular range of changing input parameters. For example, sensors work correctly within limited changing characteristics of the sensitive layer under gas influences. Due to the influence of internal factors in the body of the sensor, such as diffusion and recombination, discarding these small changes in relation to the predominant average value is incorrect and produces erroneous results.

Taking into account the periodic changes surrounding the predominant average value of the potential barrier, Equation 2 describes and allows analysis of processes in the sensitive layer of a sensor, and is free from the limitations described above.

$$\frac{\partial^2 q}{\partial t^2} - G \cdot (Eo - Ex) \cdot q = 0 \quad \text{(Equation 2)}$$

Where q is the charge, G is the conductance constant, Eo is the amplitude of the internal electric field, and Ex is the amplitude of the electric field at the boundary of the microcrystal which prevents carriers from moving freely.

Equation 2 can be simplified to an analysis of a second order differential equation in the following form:

$$\frac{\partial^2 q}{\partial t^2} + \lambda \cdot p(t) \cdot q = 0 \quad \text{(Equation 3)}$$

Where lambda, $\lambda$, is some constant, p(t) is a function of time which does not greatly vary with its average value. The function p(t), can be then rewritten as:

$$p(t) = \alpha^*(1 + \mu^* f(t)) \quad \text{(Equation 4)}$$

where alpha, $\alpha$, and mu, $\mu$ are constants and $\mu < 1$ and f(t) is a periodic function of t with an angular frequency, omega, $\omega$, for which:

$$\int_0^\omega f(t)dt = 0 \quad \text{(Equation 5)}$$

If $\alpha^*\lambda < 0$, then at a small enough $\mu$ there exists a place of instability.

For $\alpha^*\lambda > 0$, Equation 3 can be written in the form below (Equation 6), which describes the range of stability and only in this range can solutions be predicted and calculated.

$$\frac{\partial^2 q}{\partial t^2} + \lambda^2 \cdot (1 + \mu \cdot f(t)) \cdot q = 0 \quad \text{(Equation 6)}$$

The equation above can be solved using numerical approximation methods.

Figure 6:
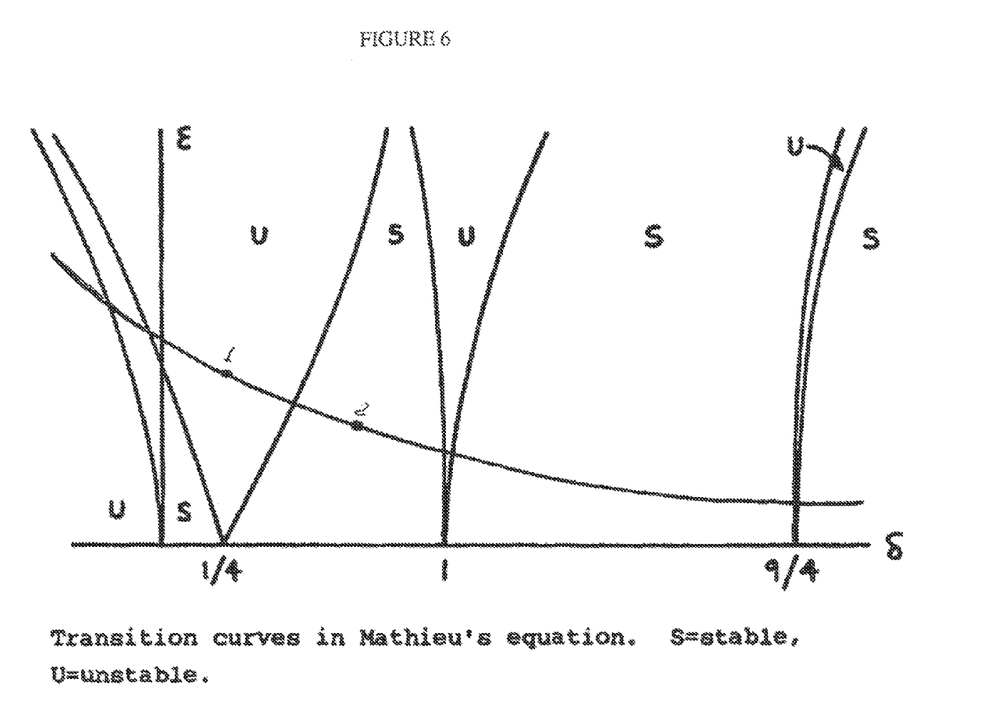
FIG. 6 shows transition curves in Mathieu's equations demonstrating areas of stability and instability according to one implementation of the invention.

As a result, it is possible to determine domains of dynamic stability and instability separated by the occurrence of resonant oscillations, in which the amplitude is raised to detectable levels. Exemplary domains of dynamic stability and instability are shown in FIG. 6.

The following observations, reasoning and conclusions are made:

1. Under the influence of flow of gas on the reactive layer of a sensor, the value of the potential barrier does not change gradually with a change in concentration; instead there exist domains of dynamic stability, where parameters can be predicted and domains of dynamic instability, where parameters are unpredictable.

2. Only within domains of stability, it is possible to determine the influence of the external factors to the sensors' sensitive layer.

3. Since the domains of stability and instability possess varying widths, and can be regulated by changing certain parameters of the system, such as temperature, pressure, etc., the method provides a way to determine desired domains for different applications.

4. Measurement procedures within individual areas of dynamic stability can be established and also allow to travel between domains under control of certain parameters and conditions.

5. Comparing the domains of stability and instability for different gases produces the ability to perform selective analysis of the gases in the mixture.

6. The boundaries between zones of dynamic stability and instability can be found by scanning and detecting increasing amplitudes of oscillations in the diapason of the changing measurement parameters.

7. Detrimental factors simply deform the widths of domains of stability and instability without destroying them and are also taken into account in the method.

8. Each gas is described by a differential equation. A gaseous mixture may be described by a system of differential equations. The individual equations and the system of equations may be solved by conventional methods.

A device implementing the proposed method works as follows. An investigated gaseous mixture, for example the exhaled breath from a patient, is prepared and collected in a Gas Preparation Unit of the device, before processing. One purpose of the Gas Preparation Unit is to promote conditions such that the investigated gaseous mixtures at any time will be measured under reproducible or consistent conditions. The pressure, volume and temperature of the gaseous mixture can vary within the Gas Preparation Unit. Variations may be regulated with the aid of a microprocessor. Equilibrium, in many cases, is preferably achieved before processing of any gas sample.

A prepared gaseous mixture is then passed to a Measurement Assembly, which serves to determine the concentration of different components in the gaseous mixture.

Internal conditions inside the Measurement Assembly, the control and regulation of various parameters, and influences on the process of passing the gases through the sensors, such as air quality, pressure of the gaseous mixture (sample), temperature of the sensing layer, speed at which the gaseous mixture (sample) is delivered to the sensing layer of the sensor, and the quality of the gaseous mixture (sample) itself, etc., are preferably regulated by one or more Control Units, which use the developed algorithm thus realizing the method. After measurement, the processed gaseous mixture is expelled from the Measurement Assembly, preparing the unit for a subsequent measurement.

The Measurement Assembly includes a predetermined number of sensors, which react with individual components of the gaseous mixture. The sensors' outputs, a series of analog signals, are then passed to a Data Acquisition Unit for amplification, filtration and digitization by an Analog-to-Digital Converter (ADC). Once digitized, the prepared data is transferred to a Data Consolidation Unit.

The Data Consolidation Unit serves to collect, store, and transfer information from each individual sensor to the microprocessor upon receiving a request. This allows for the consolidation and synchronization of individual subsystems, preventing the loss of data and increasing the dependability at the device. A data stream then leaves the Data Consolidation Unit directed for processing in the Control Unit. The Control Unit may be considered a large unit because it may be comprised of various subsystems. These subsystems are responsible for, for example, performing data conversion, providing internal communication between subsystems and producing necessary commands to accomplish device functionalities.

The DSP-based Data Processing Unit (DPU) functions to perform the actions of the Control Unit and houses the algorithm that controls the work of all subsystems in the device. The DPU also houses the algorithm to process the gathered data, thus realizing the proposed method. The DPU may communicate directly with the Control Unit and preferably shares data produced by the Data Consolidation Unit. The Control Unit performs, controls, and regulates the functionalities of the device. The functions of the Control Unit may include:

1. Receives processes, communicates and transfers data to the different units through a common interface. Achieved results are gathered and saved to a database and may be displayed in some form relatively soon after successful measurement and processing. The display may take the form of an indicator, light, flashing of a light, a digital result, text-based message, email notification, etc.

2. Controls actions performed by the electro-mechanical modules such as the pump, heater, piston, etc. The Control Unit receives and analyzes the signals from various mechanisms and performs the necessary actions and responses according to built-in application software.

3. Ensures synchronization of electronic blocks and subsystems.

The Control Unit is a multifunctional unit, which includes not only standard components, but also preferably contains an original Custom Logic Block. This block has original design circuitries for detecting areas of stability and instability in the changing parameters of the gaseous mixture as predicted by the described methods. Circuitries and their functionalities are described below. The Custom Logic Block is capable of managing data in 3D Space and in three or more dimensions when performing calculations or computations. Further, the Custom Logic Block is capable of treating a system of solutions for a plurality of unknown functions in addition to solving for an individual unknown function.

Independent modules, measurement tools and/or supplemental devices, when needed, are connected through the interface to the device. The device may include subassemblies and application software for calculating, locating and determining the boundaries of domains of stability and instability as described herein. Boundaries may be determined by analyzing some or all of the output data, which reflects changes in the parameters of the gaseous mixture. Furthermore, the subsystems used in the Control Unit insure reliability and dependability as well as provide ways to troubleshoot and diagnose the device in its entirety. The major units and their constraints are described below.

Figure 4:
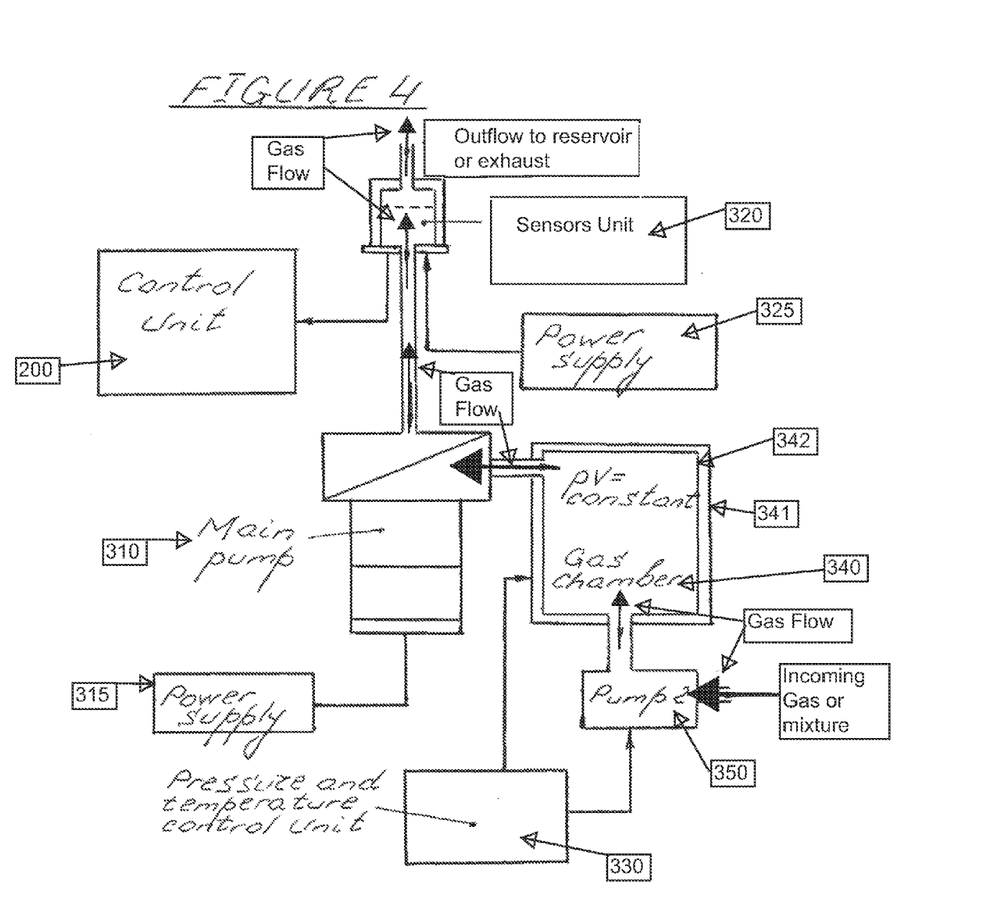
FIG. 4 shows a block diagram of a gas preparation unit according to one implementation of the invention

The Gas Preparation & Measurement Assembly Unit, 300, shown in FIG. 2, works in the following manner according to one implementation of the invention—with reference to FIG. 4 which shows the detailed structure of the Gas Preparation & Measurement Assembly with a sensor. A gaseous mixture, such as exhaled breath, is pumped with pump 2, 350, to the gas chamber, 340, as shown in FIG. 4.

The pressure and volume of the gaseous mixture in the gas chamber, 340, is regulated by, for example, a change in a position of a piston (not shown). The heating element, located in Pressure and Temperature Control subsystem, 330, built to work with the Gas chamber, 340, heats the mixture in the chamber to an assigned or designated temperature.

The gas chamber, 340, is comprised of two cylinders, one, 342, inside the other, 341. The double walls and the inner cavity prevent or reduce the exchange of heat with the surroundings. A valve (not shown) prevents the gaseous mixture from leaving the gas chamber, 340, allowing the mixture to reach equilibrium, i.e., PV=constant at an assigned temperature. Then, the valve is opened, allowing the mixture to move into the Sensors Unit, 320, for processing. The output signal of the Sensors Unit, 320, is then passed to the Control Unit, 200, while the gaseous mixture itself is exhausted to prepare the Sensor Unit, 320, for subsequent measurements.

Figure 5:
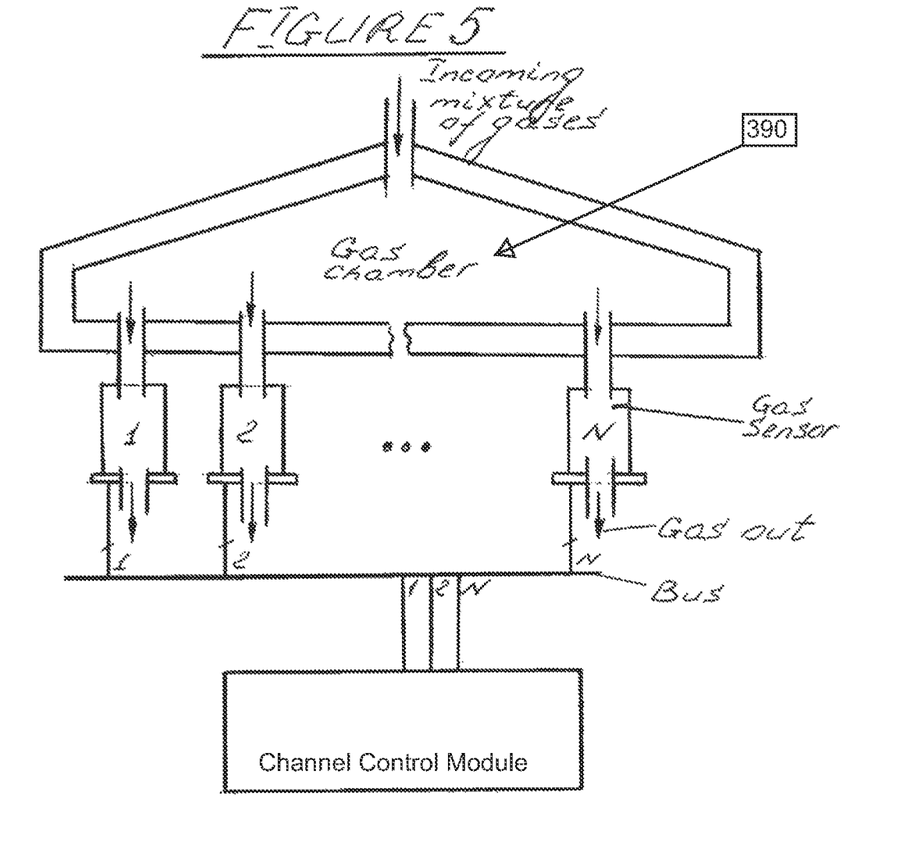
FIG. 5 shows a block diagram of a gas preparation unit assembly for a mixture of gases according to one implementation of the invention.

If a mixture of gases is being measured, then the Sensors Unit, 320, is modified according to the assembly of the Sensors Unit, 390, illustrated in FIG. 5. The Sensors Unit, 390, has a given number of sensors 1, 2, N, each of which is configured for the detection of a particular gas. The configuration for the detection of a specific gas requires the heating of the sensitive layer within a sensor to a temperature, which corresponds with the temperature at which the specific gas is most active. Each particular gas has its own one or more optimal temperatures or temperature ranges. The heating of the sensing layer inside the sensor is achieved through the utilization of an internal, built-in heating element (not shown) in the sensor.

The speed with respect to time with which the gaseous mixture enters the Sensors Unit, 320, the time the gaseous mixture is in contact with the sensing layer of a sensor and other parameters are regulated, for example, by adjusting amount of gas and gas flow being delivered to the sensor housing. The gas which passes through or over the sensor, for example, sensor #1 of Sensor Unit 390 in FIG. 5, is collected in a reservoir (not shown). This gas can be utilized for further analysis, such as for determining the composition of the mixture or simply can be released back into the surroundings. The sensors' output signals—analog signals changing with respect to time—are detected and processed in the electronic subsystem(s) of the proposed device.

Figure 1A:
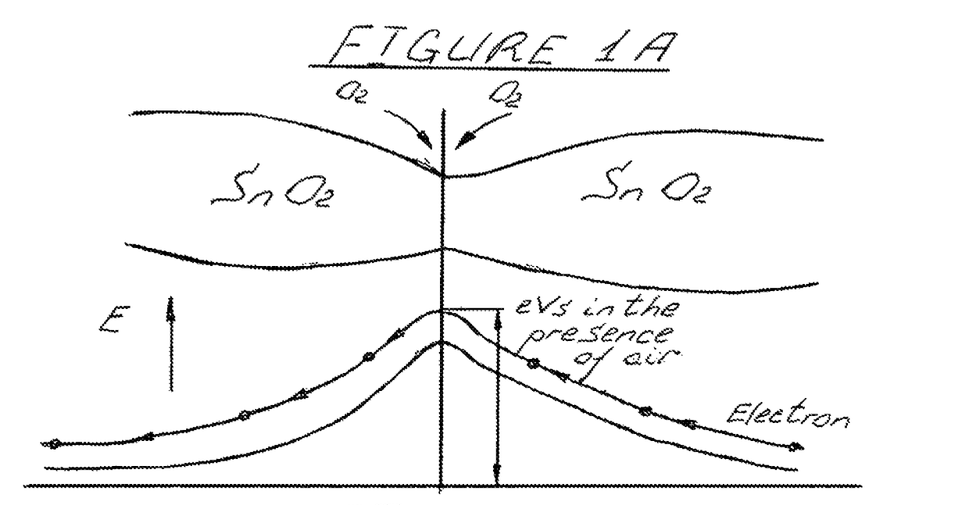
FIG. 1A shows the mechanism without the presence of gas.
Figure 1B:
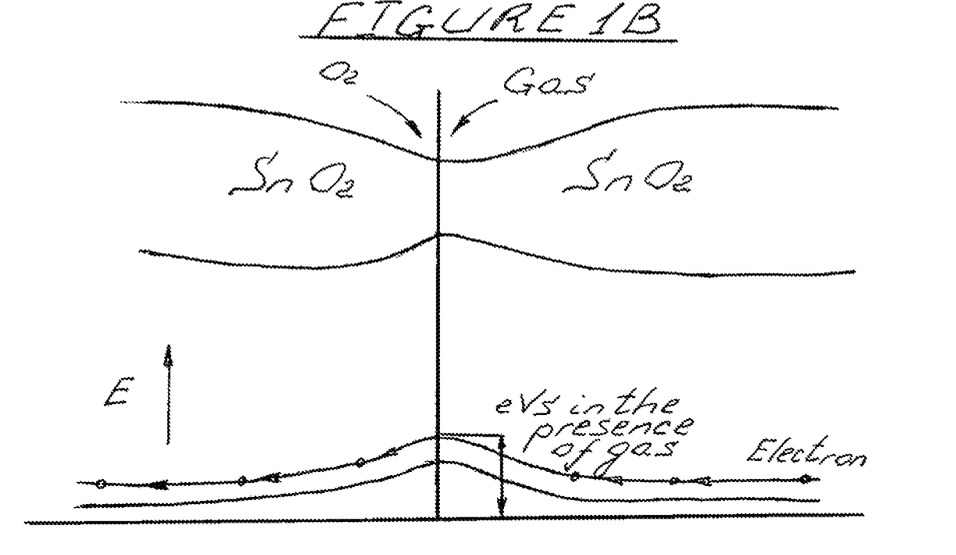
FIG. 1B shows the mechanism with the presence of gas.
Figure 2:
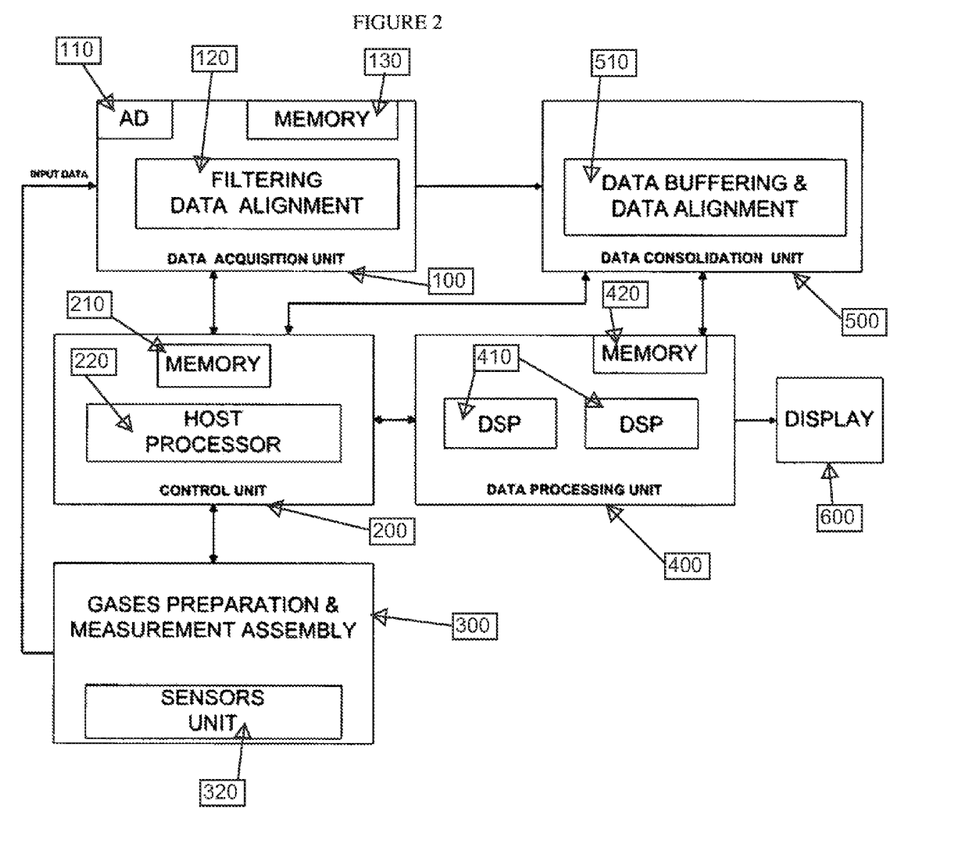
FIG. 2 shows a block diagram of a device for measuring and analyzing exhaled gases based on one implementation of one of the methods disclosed herein.
Figure 3:
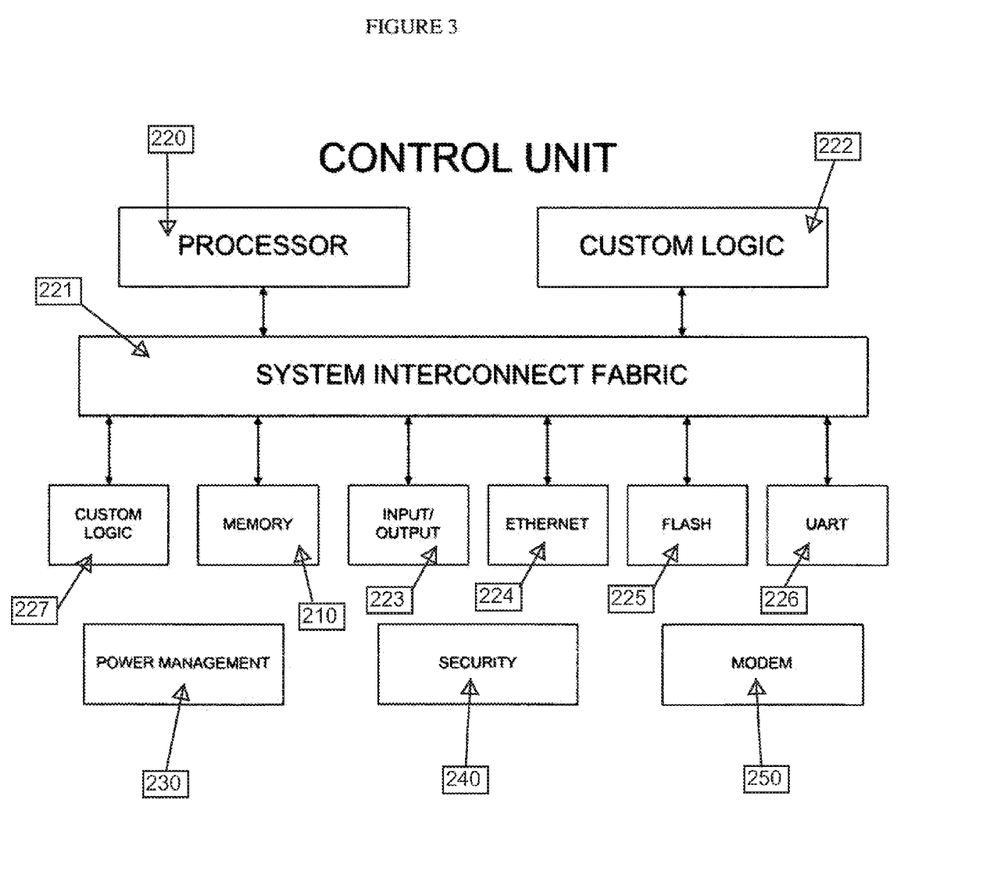
FIG. 3 shows a block diagram of a control unit, which includes a custom logic block according to one implementation of the invention. There are subassemblies conforming to an original algorithm to process the gathered information and perform functionalities of a device involving methods described herein.

With reference to FIGS. 2-5, the electronic subsystems work in the following manner according to one implementation of the invention. The outputs of the sensors, in form of analog signals, are transferred to the inputs of a Data Acquisition Unit, 100 in FIG. 2. In the Data Acquisition Unit, signals are amplified, filtered, and' converted to a digital form. An Analog-to-Digital Converter, 110, is used. Then the processed signal enters the Data Consolidation Unit, 500, where FIFOs and other storage elements are used to save and synchronize the data streams produced inside internal subsystems. This ensures the functionality and reliability of the processor, the Control Unit, 200, and the entire device. FIG. 3 shows the structure of an exemplary Control Unit, which is responsible for controlling the major processes and functionalities of different components and the device itself, including power distribution, security, mechanical arms control, valve operations, piston movement, etc. The Control Unit also treats and prepares information to be transferred between the internal units.

Original Custom Logic, 222, implemented in the Control Unit, is involved in the detection of the boundaries of stability and instability—such as the boundaries, which separate stable and unstable regions such as those shown in FIG. 6. With reference to FIG. 3, the indicated subsystem includes an asynchronous block, 227, that operates the application software to determine the domains of stability and instability through the analysis of the changes in the output parameters of the gaseous mixture as outlined by the methods described herein. The Control Unit subsystem also includes time-dependent logic components (not shown), switching capacitors and other elements used to determine and analyze the characteristics of oscillation occurring at the boundaries of domains of stability and instability.

The Data Processing Unit, 400, shown in FIG. 2 includes an implemented algorithm that realizes one embodiment of a proposed method as well as algorithms that utilize proper operations of the device and appropriate software applications to insure continuity, reliability and dependability of the individual subsystems and their interaction within the device. Furthermore, the algorithms define and control the data stream(s) within the device, transferring the data through the interface. Standard protocols such as universal asynchronous receiver/transmitter UART (serial), 226, Ethernet (TCP/IP), 224, Flash, 225, and others can be implemented to aid and utilize the information exchange.

Sampling, sensing and calculation of values related to a concentration of a gas may be repeated so as to perform uninterrupted monitoring of a gas. Such repeating may be done as frequently as possible for continuous monitoring, or may be done at predefined intervals so as to provide intermittent updates of values related to a gas concentration or intermittent monitoring of a gas. Time may be utilized as a parameter in processing to assist in determining if or when the system is in the stable or unstable domain at the general instant of when the measurement occurs.

Simultaneous measurement of various gases in a gaseous mixture can be made utilizing the methods described herein by distributing incoming gas into different channels each equipped with its own sensor for the targeted gas and then using the methods described herein to calculate the concentration of each gas in its respective channel. For example, one channel could measure a concentration of nitrogen, and a second channel could measure a concentration of oxygen.

In one implementation, ambient air is pumped into the system to clear the sensor area of measured gases and prepare the sensing layer of the sensor for subsequent measurements, reducing the time between measurements. The methods described herein allow for monitoring the state of the system in real time when a measurement is being performed. In another implementation, the methods described herein do not require prior preparation or calibration of the sensors or system in order to take a measurement, which is an improvement over other methods and devices of measurement of gases, vapors and liquids.

Although the present invention has been described with reference to specific exemplary embodiments, it will be evident that modifications and changes can be made to these embodiments without departing from the broader spirit of the invention. Accordingly, the specification and drawings are to be regarded in an illustrative sense rather than in a restrictive sense.

Similarly, while certain exemplary embodiments have been described and shown in the accompanying drawings, it is to be understood that such embodiments are merely illustrative and not restrictive of the broad invention and that this invention is not limited to the specific constructions and arrangements shown and described therein, since various other modifications may be made according to the abilities of those ordinarily skilled in the art upon studying this disclosure. The disclosed embodiments may be readily modifiable as facilitated by enabling technological advancements without departing from the principals of the present disclosure.

We claim:

1. A device for detecting a concentration of a component of a sample, the device comprising:
    a trapping chamber for temporarily containing a volume of the sample;
    a sensing chamber, wherein the sensing chamber is capable of being exposed to a portion of the sample, wherein the sensing chamber includes a sensing surface of a sensor, and wherein the sensor is capable of and programmed with instructions to generate a change in current as a result of interaction with the component of the sample;
    a memory configured with instructions that cause the device to:
        make a computation related to Mathieu's Equation with a value for each initial condition of Mathieu's Equation to determine whether a value associated with the change in current is in a stable domain;
        when the value associated with the change in current is not in a stable domain, varying one or more of the initial conditions of Mathieu's Equation, and
        trigger a repeating of determining whether the value associated with the change in current is in a stable domain.

2. The device of claim 1, wherein the device further comprises:
    a valve located between the trapping chamber and the sensing chamber, and wherein the valve is associated with allowing a portion of the sample into the sensing chamber;
    a control unit configured with instructions to:
        manipulate an initial condition of Mathieu's Equation;
        operate the valve associated with allowing the portion of the sample into the sensing chamber; and
        interact with the memory and electrical output associated with the sensor or sensor surface.

3. The device of claim 1, wherein the sample is a gas, vapor or liquid.

4. The device of claim 1, wherein a temperature of the sensor is set to a different temperature from that as used during a previous determining of the concentration of the component of the sample.

5. The device of claim 1, and wherein the sample is a gas or vapor, and wherein a pressure of the trapped volume of sample is varied from a pressure of the trapped volume of sample as measured during a previous determining of the concentration of the component of the sample.

6. The device of claim 1, wherein Mathieu's Equation is of a form:

$$\frac{\partial^2 x}{\partial t^2} + \lambda^2 \cdot (1 + \mu \cdot f(t)) \cdot x = 0$$

where lambda, $\lambda$, represents a numeric constant, where mu, $\mu$, represents another numeric constant, and where t represents time.

7. The device of claim 1, wherein the device is programmed to contain the volume of the sample in the trapping chamber for a sufficient time so that a substantial portion of the trapped volume of the sample is substantially isolated from an influence of an atmospheric temperature.

8. The device of claim 1, wherein the containing of the volume of the sample in the trapping chamber includes trapping the volume of the sample sufficiently so as to avoid a measurable amount of a contaminant in the sample.

9. The device of claim 1, wherein a stable domain is a numeric domain where values associated with the change in current can be predicted in accordance with the said Mathieu's Equation, and wherein an unstable domain is a numeric domain where a resulting value associated with the change in current is unreliable.

10. The device of claim 1, wherein the determining the concentration of the component of the sample includes the use of parametric vibrations when the value associated with the detected current is approximately at a border between a stable domain and an unstable domain.

11. The device of claim 1, wherein the instructions further include:
- using a unique identifier of, or a particular value associated with, the component of the sample to distinguish the component from one or more other components of the sample.

12. The device of claim 1, wherein the sample includes a second component, and wherein the instructions further include:
- for the second component, making a computation related to Mathieu's Equation with a value for each initial condition of Mathieu's Equation to determine whether a value associated with the change in current is in a stable domain;
- for the second component, when the value associated with the change in current is not in a stable domain, varying one or more of the initial conditions of Mathieu's Equation, and
- for the second component, triggering a repeating of determining whether the value associated with the change in current is in a stable domain; and
- determining the concentration of the second component of the sample using the value associated with the detected current with respect to the second component.

13. The device of claim 1, before using Mathieu's Equation, selecting values for the initial conditions for Mathieu's Equation such that when determining the value associated with the detected current, the value associated with the change in current is in a stable domain.

14. A method for determining a concentration of a component of a sample, the method comprising:
- [1] trapping a volume of the sample in a chamber;
- [2] exposing the sample in the chamber to a sensor;
- [3] detecting a change in current as a result of interaction of the sample with the sensor;
- [4] capturing a copy of the value associated with the change in current;
- [5] using logic related to Mathieu's Equation with a value for each initial condition of Mathieu's Equation, determining when a value associated with the detected current is in a stable domain, wherein the values associated with the initial conditions are related to conditions of the sample in the chamber;
- [6] when the value associated with the detected current is not in a stable domain, varying one or more of the initial conditions of Mathieu's Equation, and repeating the determining until the detected current is determined to be in a stable domain; and
- [7] determining the concentration of the component of the sample using the captured copy of the value associated with the change in current.

15. The method of claim 14, wherein the logic related to Mathieu's Equation is logic involving three or more dimensions.

16. The method of claim 14, wherein a temperature of the sensor is varied in step [6] from a temperature from that used during a previous determination of whether the value associated with the detected current is in a stable domain.

17. The method of claim 14, wherein a pressure of the sample is varied in step [6] from a pressure related to the trapped volume of sample from that pressure used during a previous determination of whether the value associated with the detected current is in a stable domain.

18. The method of claim 14, wherein the method further comprises:
- [8] displaying a value related to the concentration of the component of the sample using the captured copy of the value associated with the change in current; and
- repeating steps [1] through [8] until a condition to stop said repeating is detected.

19. The method of claim 14, wherein the method further comprises:
- after step [4], passing ambient air over the sensor to prepare the sensor for a subsequent measurement.

20. The method of claim 14, wherein the using logic related to Mathieu's Equation includes logic involving one or more of: real-value variables, a periodic function, a discontinuous function with one or more solutions in a restricted area, or a finite interval measurement function.

* * * * *